US011324561B2

(12) United States Patent
Fan et al.

(10) Patent No.: US 11,324,561 B2
(45) Date of Patent: May 10, 2022

(54) REMOTE MANIPULATOR SYSTEM AND METHOD FOR OPERATING A REMOTE MANIPULATOR SYSTEM

(71) Applicant: KARL STORZ SE & CO. KG, Tuttlingen (DE)

(72) Inventors: Chunman Fan, Tuttlingen (DE); Sebastian Wagner, Tuttlingen (DE)

(73) Assignee: KARL STORZ SE & CO. KG, Tuttlingen (DE)

( * ) Notice: Subject to any disclaimer, the term of this patent is extended or adjusted under 35 U.S.C. 154(b) by 679 days.

(21) Appl. No.: 16/288,261

(22) Filed: Feb. 28, 2019

(65) Prior Publication Data

US 2019/0269475 A1 Sep. 5, 2019

(30) Foreign Application Priority Data

Mar. 1, 2018 (DE) ...................... 10 2018 104 714.2

(51) Int. Cl.
*A61B 1/00* (2006.01)
*A61B 34/00* (2016.01)
(Continued)

(52) U.S. Cl.
CPC .......... *A61B 34/74* (2016.02); *A61B 1/00149* (2013.01); *A61B 1/3132* (2013.01);
(Continued)

(58) Field of Classification Search
CPC ..... A61B 34/74; A61B 34/37; A61B 1/00149; A61B 1/3132; A61B 2034/301; A61B 2034/302
See application file for complete search history.

(56) References Cited

U.S. PATENT DOCUMENTS

2002/0058929 A1  5/2002  Green
2016/0249984 A1  9/2016  Janssen
(Continued)

FOREIGN PATENT DOCUMENTS

DE         69312053 T2    10/1997
DE       102014006264 A1  11/2015
(Continued)

OTHER PUBLICATIONS

Search and Examination Report for corresponding Great Britain Patent Application No. GB1902204.5 dated Jul. 17, 2019.
(Continued)

*Primary Examiner* — Timothy J Neal
*Assistant Examiner* — William B Chou
(74) *Attorney, Agent, or Firm* — Jason H. Vick; Sheridan Ross, PC

(57) ABSTRACT

A remote manipulator system according to the invention for carrying out manipulations in a body-internal cavity comprises a manipulator apparatus with a motor-driven actuator mechanism for moving at least two endoscope apparatuses that are insertable through a respective access opening into the body-internal cavity, said endoscope apparatuses each having an elongate shaft (3), wherein the at least two endoscope apparatuses are each displaceable along a longitudinal direction and pivotable about a pivot point (10) defined by the respective access opening, an operating apparatus (21, 71) with at least two control elements (22, 22', 22", 33, 72, 72', 72", 73), which each have an elongate shaft (23, 23'), wherein the at least two control elements (22, 22', 22", 33, 72, 72', 72", 73) are each, in manual fashion, displaceable in the direction of a longitudinal axis and pivotable about a pivot point (30), and a controller (75) which is embodied to detect a respective longitudinal displacement and pivot movement of the at least two control
(Continued)

elements (22, 22', 22", 33, 72, 72', 72", 73) and actuate the manipulator apparatus (1) in such a way that the movements of the endoscope apparatuses correspond to those of the at least two control elements (22, 22', 22", 33, 72, 72', 72", 73), wherein the operating apparatus (21, 71) is embodied in such a way that a relative position of the pivot points (30) of the control elements (22, 22', 22", 33, 72, 72', 72", 73) is adjustable.

17 Claims, 6 Drawing Sheets

(51) Int. Cl.
  *A61B 34/37* (2016.01)
  *A61B 1/313* (2006.01)
  *A61B 34/30* (2016.01)

(52) U.S. Cl.
  CPC ........ *A61B 34/37* (2016.02); *A61B 2034/301* (2016.02); *A61B 2034/302* (2016.02)

(56) References Cited

U.S. PATENT DOCUMENTS

| | | |
|---|---|---|
| 2016/0374771 A1 | 12/2016 | Mirbagheri et al. |
| 2018/0049830 A1 | 2/2018 | Yates et al. |

FOREIGN PATENT DOCUMENTS

| | | |
|---|---|---|
| EP | 1131004 B1 | 10/2009 |
| WO | WO 93/13916 | 7/1993 |
| WO | WO 2007/146984 | 12/2007 |
| WO | WO 2012/044334 | 4/2012 |
| WO | WO 2014/176403 | 10/2014 |
| WO | WO 2016/030767 | 3/2016 |
| WO | WO 2017/210098 | 12/2017 |

OTHER PUBLICATIONS

Search Report for corresponding German Patent Application No. 102018104714.2, dated Oct. 24, 2018.

REMOTE MANIPULATOR SYSTEM AND METHOD FOR OPERATING A REMOTE MANIPULATOR SYSTEM

CROSS-REFERENCE TO RELATED APPLICATIONS

This application claims the benefit under 35 U.S.C. 119(a) to German Patent Application No. 10 2018 104 714.2, filed Mar. 1, 2018, the disclosure of which is incorporated herein by reference in its entirety.

BACKGROUND

The present invention relates to a remote manipulator system for carrying out manipulations in a body-internal cavity of a human or animal body according to the claims appended hereto, and to a method for operating such a remote manipulator system.

Actuating a plurality of surgical instruments with high precision over a long period of time is often necessary within the scope of surgical interventions. Robotic surgical systems have been developed to unburden the surgeon, improve the precision of the surgical manipulations carried out during an intervention and shorten the duration of the surgical intervention. Such a robotic surgical system comprises an electronically controlled manipulator apparatus for moving, in motor-driven fashion, the surgical instruments required during the intervention, and an operating apparatus by means of which the surgeon can control the movement of the surgical instruments. By way of example, the operating apparatus may comprise one or more operating levers (joysticks) or other control elements that are movable by hand, as a result of the actuation of which the movement of the surgical instruments can be controlled. By way of example, the manipulator apparatus may have one or more manipulator arms that are designed to move surgical instruments with a plurality of degrees of freedom. Such a robotic surgical system can also be designed for controlling a surgical intervention from a remote location and it is also referred to in this case as a remote manipulator system, remote surgery system or telepresence system.

Robotic surgical systems that can also be designed for carrying out endoscopic interventions are known from EP 1 131 004 B1, WO 2007/146984 A2 and WO 2014/176403 A1, for example. In the minimally invasive surgical system disclosed in WO 2012/044334 A1, a position of a sensor element assembled on a part of a human hand, such as, for instance, a finger, is tracked by a hand tracking system. A system control parameter is established on account of the position of the part of the human hand and the operation of the minimally invasive surgical system is controlled by means of the system control parameter.

According to DE 10 2014 006 264 A1, a robotic system comprises three robots, which are fastened laterally to an operating table and are each equipped with a tool and are actuated by way of a control unit. For the purposes of controlling the robots, the robotic system comprises a guiding object, the movements of which are detected by the control unit in order to track corresponding movements with the end effectors of the tools, which could be surgical grippers, scissors or scalpels, for example. A joystick, a clamp or the hand of the user themselves can be used as guiding object.

The movement possibilities of the employed endoscopic instruments are often restricted by additional conditions in endoscopic surgical operations. Thus, for example, the abdominal wall is usually lifted by introducing an insufflation gas into the abdominal cavity in the case of laparoscopic operations, and this creates a work space for the surgical instruments. The surgical instruments, which are embodied as laparoscopic instruments with an elongate shaft in each case, are introduced into the work space through incisions (cuts) in the abdominal wall. Here, the incisions define pivot points, which restrict the movement degrees of freedom of the laparoscopic instruments. However, in many known robotic surgical systems, the manually movable control element assigned to an endoscopic instrument is also movable in such a way that a corresponding movement of the endoscopic instrument is precluded by the aforementioned movement restrictions. This makes intuitive operation more difficult. Therefore, such robotic surgical systems require a long learning phase, and there often is no shortening of the duration of the operation.

DE 693 12 053 T2 has disclosed a remote control system for manipulating an object arranged in a work space at a work site by an operator from an operator control panel situated at a distance from the work site. A manipulator is situated at the operating site, said manipulator having a movable manipulator arm with an end effector for the purposes of manipulating the object. The operator control panel has a movable control mechanism that is operated by hand. Further, a servomechanism is provided, which couples the movable control mechanism that is operated by hand to the manipulator arm for the purposes of remotely controlling the manipulator arm. The controller has a right and a left control arm, which are provided with the same degree of freedom as the connected manipulator arms. For laparoscopic surgery, a pivot point is situated substantially level with the abdominal wall through which the manipulator extends. Here, the pivot movement about the pivot point is created by simultaneous lateral movement of an external operating end of the manipulator and a pivot movement of the manipulator arm. However, an intuitive operation was often found to be difficult in this case, too.

It is an object of the present invention to specify a remote manipulator system for carrying out manipulations in a body-internal cavity of a human or animal body, and a method for operating such a remote manipulator system, wherein the aforementioned disadvantages can be avoided to the greatest possible extent.

This object is achieved by an apparatus according to the claims appended hereto and by a method according to the claims appended hereto.

Advantageous developments of the invention emerge from the dependent claims.

A remote manipulator system according to the invention is embodied to carry out manipulations in a body-internal cavity of a human or animal body, in particular for carrying out endoscopic surgical interventions within the body-internal cavity. To this end, the remote manipulator system comprises a manipulator apparatus with a motor-driven actuator mechanism that is embodied to move, in motor driven fashion, at least two endoscope apparatuses that are insertable into the body-internal cavity through a respective access opening. The body-internal cavity can be a natural cavity, or else a cavity that was artificially created or enlarged by means of insufflation with gas, for example, said cavity serving as a work space for the manipulations. Here, an "endoscope apparatus" denotes an endoscopic surgical instrument or an endoscope optical unit. The endoscope apparatuses can be embodied as part of the manipulator apparatus and can be securely or detachably connected to the latter. However, the endoscope apparatuses could also be endoscopic instruments or an endoscope optical unit that can be used independently of the manipulator apparatus as well, for instance in the case of interventions that are carried out manually. The endoscope apparatuses each have an elongate shaft, wherein an end effector, a surgical tool such as a gripper, scissors or an RF electrode, for example, can be arranged at the distal end of the shaft. Usually, an endoscope lens for recording an endoscopic image of a portion of the body-internal cavity is arranged at the distal end of the shaft of an endoscope optical unit.

The access openings of the at least two endoscope apparatuses are different access openings that are arranged at a distance from one another. The access openings can be natural access openings or artificially created access openings to the body-internal cavity. In the case of laparoscopic interventions, the access openings are usually created by incisions in the abdominal wall, wherein a trocar tube is initially inserted into the respective incision. After removing the trocar mandrel that was inserted in the trocar tube and used to carry out the incision, the respective endoscope apparatus can be pushed into the abdominal cavity through the trocar tube.

In the case of the manipulator apparatus of the remote manipulator system according to the invention, the at least two endoscope apparatuses are each, by means of the actuator mechanism, displaceable in the direction of a respective longitudinal axis of the shaft and pivotable about a pivot point defined by the respective access opening. In particular, the at least two endoscope apparatuses are rotatable about the respective pivot point, in each case about two axes that are perpendicular to one another and transverse to the longitudinal axis of the shaft. When the actuator mechanism engages at a proximal end region of an endoscope apparatus, a pivot movement about the pivot point lying in the access opening can be achieved by coordinated transverse and pivot movement of a proximal end region. Since the pivot point in laparoscopic interventions is usually defined by the trocar tube inserted into the access opening in the abdominal wall, the pivot point is also referred to as "trocar point".

Furthermore, the remote manipulator system according to the invention comprises an operating apparatus with at least two control elements that are movable in manual fashion. The control elements each have an elongate shaft, wherein the control elements are each, in manual fashion, displaceable in the direction of a longitudinal axis of the shaft and pivotable about a respective pivot point of the control element. Preferably, at least two control elements are respectively pivotable about two axes that are perpendicular to one another and transverse to the longitudinal axis of the shaft, said axes extending through the respective pivot point. By way of example, the pivot point can be defined by a ball joint or by two single-axis joints. Here, the two axes need not necessarily must; in this case, a region through which the two axes extend and which is approximately defined by the two single-axis joints is also referred to in simplified fashion as a "pivot point" within the scope of the present invention. Preferably, the same number of control elements and endoscope apparatuses are provided, with respectively one control element being assigned to one endoscope apparatus.

The at least two control elements are embodied to detect and move with a hand of a user. In particular, the control elements can each be arranged and embodied to be grasped by a hand of the user, for example a first control element to be grasped by the right hand and a second control element to be grasped by the left hand of the user. Preferably, an end region of the control elements is respectively embodied to be grasped by, and moved with, a hand of the user, for the purposes of which a manual control element can be arranged at the end of the shaft in each case. By way of example, the user can be a surgeon who is able to carry out an endoscopic intervention by means of the remote manipulator system by actuating the control elements.

Further, the remote manipulator system according to the invention comprises an electronic controller, which is embodied to detect a respective longitudinal displacement and a respective pivot movement of the at least two control elements and actuate the manipulator apparatus in such a way that the at least two endoscope apparatuses are moved in a manner corresponding to the movement of the at least two control elements. In particular, the controller is configured for each endoscope apparatus to be moved in a manner corresponding to the movement of the respectively assigned control element. For the purposes of detecting the movement of the control elements, the operating apparatus can be equipped with corresponding linear and rotary encoders or other suitable sensors, the signals of which can be detected and processed by the controller, or provision can be made of, for example, an optical tracking device for tracking the position and, optionally, the orientation of the manual control elements. Likewise, the controller is embodied in a manner known per se for actuating the motor-driven drives of the actuator mechanism for moving the surgical instruments in order to bring about a movement of the endoscope apparatuses in a manner corresponding to the movement of the control elements brought about by the user. In particular, the distal end regions of the endoscope apparatuses or the end effectors are each controlled in a manner corresponding to the movement of the manual control elements. Here, the movement of the end effectors can have the same magnitude as that of the manual control elements, or it may differ by a fixed scaling factor. The shafts of the at least two endoscope apparatuses can each be pivoted through the same angle and can always be oriented in relation to one another with the same angles, like the shafts of the control elements.

According to the invention, the operating apparatus is embodied in such a way that a relative position of the pivot points of the control elements is adjustable. In particular, the distances between the pivot points of the control elements or the spatial relationship of the pivot points in relation to one another may be adjustable. Consequently, the pivot points about which the shafts of the control elements are pivotable are not fixedly predetermined but can also be positioned in relation to one another and, as a result thereof, can be adapted to a respective situation. By way of example, this renders it possible to set the pivot points of the control elements of the operating apparatus in different operation situations, for instance on account of different physiological conditions of the patients, in such a way in each case that the relative position of said pivot points of the control elements corresponds to the relative position of the pivot points of the endoscope apparatuses and hence, for example, the relative position of the trocar points. By way of example, the arrangement of pivot points or trocar points is determined by the type of the employed endoscopic instruments, by the position of an operating field in the work space and by the curvature of the abdominal wall. Consequently, an arrangement of the pivot points of the control elements that corresponds to the actual situation during the endoscopic intervention can be created.

As a result of a relative position of the pivot points of the control elements of the operating apparatus being adjustable and, in particular, being able to be selected in a manner corresponding to the arrangement of the trocar points, it is possible to achieve a spatial relationship of the at least two endoscope apparatuses that corresponds to the spatial relationship of the control elements, even in different operating situations, and maintain said spatial relationship during a movement, in particular a spatial relationship of the end effectors that corresponds to the spatial relationship of the manual control elements. The spatial relationship comprises a relative spatial position, wherein a scaling factor may be provided, and a relative spatial orientation of the shafts of the controllers and of the endoscope apparatuses. Consequently, the shafts of the at least two endoscope apparatuses can be arranged at the same angles in relation to one another in each case as the shafts of the correspondingly assigned control elements, and the distance vectors between the end effectors of the at least two endoscope apparatuses can be oriented relative to the shafts with the same angles as the distance vectors between the manual control elements of the respectively assigned control elements, wherein the magnitude of the distance may likewise be the same or may differ by the fixed scaling factor. In this way, the remote manipulator system is adaptable to a multiplicity of operating situations, and so the spatial arrangement of the control elements is a mapping, possibly a scaled mapping, of the arrangement of the endoscope apparatus in the work space, even in the case of a movement of the endoscope apparatuses. By way of example, the operating apparatus may comprise a monitor or projector, by means of which a recorded endoscopic image of the work space can be displayed in such a way that the orientation of the control elements in the image corresponds to the orientation of the endoscope apparatuses in the work space. This can simplify an intuitive operation of the endoscope apparatuses in the case of an endoscopic intervention.

According to a preferred embodiment of the invention, the relative position of the pivot points of the control elements of the operating apparatus is manually adjustable. By way of example, the pivot points can be defined by single-axis or multi-axis rotary joints, which are fastened to a holding mechanism that is adjustable in one or more spatial directions. The holding mechanism can be adjustable, affixable and releasable by hand. This allows the user to choose, quickly and in uncomplicated fashion, a respectively suitable arrangement of the pivot points in order to reproduce a corresponding spatial relationship of the pivot points of the endoscope apparatuses.

According to a particularly preferred embodiment of the invention, the manipulator apparatus is embodied to detect the relative positions of the pivot points of the at least two endoscope apparatuses, i.e., for example, to detect the arrangement of the trocar points. The operating apparatus is embodied to set the pivot points of the control elements in motor-driven fashion, wherein the controller is configured in such a way that the pivot points of the control elements are set in a manner corresponding to the detected positions of the pivot points of the endoscope apparatuses. By way of example, detection of the pivot points of the endoscope apparatuses can be implemented by means of appropriate sensors or a camera with an appropriate image evaluation. For the purposes of setting the pivot points of the control elements of the operating apparatus in motor-driven fashion, provision can be made of, for example, a motor-driven adjustment of a holding mechanism, ball joints or multi-axis rotary joints being fastened to said holding mechanism, said joints defining the pivot points of the control elements. This facilitates setting of the operating apparatus in a particularly simple and convenient manner, said setting being optimal for intuitive operation, even in the case of different operations or different physiological conditions.

Advantageously, the at least two endoscope apparatuses are additionally rotatable in motor-driven fashion about the respective longitudinal axis of their shaft by means of the actuator mechanism and the at least control elements are respectively rotatable in manual fashion about the longitudinal axis of their shaft. In this case, the electronic controller is embodied to detect a respective rotation about the longitudinal axis of the shafts of the at least two control elements and actuate the manipulator apparatus in such a way that there is a corresponding rotation of the respectively assigned endoscope apparatus about a longitudinal axis of its shaft. As a result of this, the use options of the remote manipulator system can be extended.

Preferably, a tool is arranged at the distal end of the shaft of at least one of the endoscope apparatuses, said tool having at least one actuation degree of freedom, and a manual control element is arranged at the end of the shaft of a control element, which is assigned to this endoscope apparatus, said manual control element having an actuation element for controlling the actuation degree of freedom. By way of example, the tool can be a surgical gripper, a pair of forceps or a pair of scissors, or else a radiofrequency electrode that is able to be pushed out of the shaft, wherein the movement of at least one movable element of the tool can be controlled by the actuation element of the control element. In particular, the actuation element can reproduce the actuation degree of freedom of the tool. The at least one tool can also be arranged at the end of the shaft and be able to be angled in relation thereto, and the corresponding manual control element can be arranged at the shaft of the control elements in such a way that it is able to be angled by hand, and so the angling movement of the tool can also be controlled with the aid of the manual control element. This simplifies an intuitive operation of the tool.

According to a preferred embodiment of the invention, the operating apparatus has a blocking or securing mechanism, with the aid of which a control element is held in a respective position and orientation if a user has not grasped the latter or has let the latter go during the operation. This can prevent an uncontrolled movement of the associated endoscope apparatus arising as a result of an independent movement of the control element, and the safety during a surgical intervention is increased.

Preferably, the blocking mechanism is automatically activatable, with the electronic controller being configured in such a way that a control element is automatically blocked if the latter, or the corresponding manual control element, is not grasped by the user or if the user has let this go. By way of example, to this end, a corresponding sensor can be provided on the control element, the signal of said sensor being able to be used for identification as to whether the control element has been let go by the user and blocking has to be activated. This further increases the safety in a surgical intervention.

Advantageously, provision can be made for a size and a form of the body-internal cavity, in which the endoscope apparatuses can be inserted, to be detected and for the controller and the operating apparatus to be embodied in such a way that a manual movement of the at least two control elements is restricted to a region corresponding to the body-internal cavity. This region, which corresponds to the usable work space, is also referred to as model space. By way of example, provision can be made of a camera for detecting the size and form of the cavity. The blocking mechanism, in particular, can be usable for a corresponding movement restriction. What this can achieve is that the control elements can only be used to carry out those movements which can in fact be carried out in a corresponding manner within the work space by the endoscope apparatuses. This can further simplify the intuitive operation of the remote manipulator system.

According to a preferred embodiment of the invention, the operating apparatus can have one or more calibration marks which are arranged within a spatial region in which the control elements are movable by hand, i.e., in particular, in a model space corresponding to the body-internal cavity. This allows a calibration of the sensors for detecting the movement of the control elements to be carried out. In this way, the accuracy of the control of the endoscope apparatuses, which corresponds to the movement of the control elements, can be increased.

Furthermore, it is preferable for the manipulator apparatus to have at least one further operating apparatus, which may be embodied as described above. In particular, the electronic controller according to this embodiment is configured to process signals of the plurality of operating apparatuses in such a way that each endoscope apparatus is controllable by means of exactly one control element in each case, wherein the control elements that are assigned to different endoscope apparatuses may be arranged in different operating apparatuses. For instance, a first and a second control element, which are assigned to a first and a second endoscope apparatus, may be arranged in a first operating apparatus in order to be grasped and moved by respectively one hand of a first operator, and a third and a fourth control element, which are assigned to a third and a fourth endoscope apparatus, may be arranged in a second operating apparatus in order to be grasped and moved by respectively one hand of a second operator. This can facilitate an alternating operation, and also a simultaneous operation, of the manipulator apparatus by a plurality of users.

A further aspect of the invention relates to a method for operating a remote manipulator system. The remote manipulator system comprises a manipulator apparatus with a motor-driven actuator mechanism for the motor-driven movement at least two endoscope apparatuses that are insertable through a respective access opening into a body-internal cavity of a human or animal body. The endoscope apparatuses each have an elongate shaft and are each, by means of the actuator mechanism, displaceable in the longitudinal direction of the shaft and pivotable about a pivot point defined by the respective access opening. Furthermore, the remote manipulator system comprises an operating apparatus with at least two control elements, which each have an elongate shaft, wherein the at least two control elements are each, in manual fashion, displaceable in the direction of a longitudinal axis of the shaft and pivotable about a respective pivot point. Further, the remote manipulator system may comprise an electronic controller. In particular, the remote manipulator system is embodied as described above and preferably suitable for carrying out manipulations in the body-internal cavity.

According to the method according to the invention, the pivot points of the at least two control elements are set in a manner corresponding to a spatial relationship of the pivot points of the endoscope apparatuses. For instance, the pivot points of the endoscope apparatuses can be the trocar points in the case of a laparoscopic intervention. The pivot points of the at least two control elements can be set by virtue of, for example, rotary joints defining the pivot points being correspondingly displaced and/or positioned. The displacement and/or positioning is preferably implemented in motor-driven fashion, wherein the pivot points of the endoscope apparatuses are automatically detected and the pivot points of the control elements can be automatically set accordingly. In particular, the pivot points are set in such a way that a spatial relationship of the pivot points of the at least two control element in relation to one another is the same as the spatial relationship of the pivot points of the endoscope apparatuses in relation to one another, i.e., in particular, the distances between the respective pivot points among themselves are the same in the case of the control elements as in the case of the endoscope apparatuses, or they can merely be distinguished from one another by a fixed scaling factor.

Further, a respective longitudinal displacement and a respective pivot movement of the at least two control elements are detected according to the method according to the invention, said longitudinal displacement and pivot movement being able to be carried out by hand by a user by grasping the control elements. By way of example, these movements can be detected by means of appropriately arranged linear and rotary encoders. In particular, the movements are detected automatically and the corresponding measurement values are processed by the electronic controller.

According to the invention, the manipulator apparatus is actuated in such a way that the movement of the at least two endoscope apparatuses corresponds to that of the at least two control elements. Since the spatial relationship of the pivot points of the control elements is set according to the spatial relationship of the pivot points of the endoscope apparatuses, the spacings of the distal end regions of the endoscope apparatuses, or of the respective end effectors, in particular, are the same as those of the respectively assigned control elements or manual control elements, or else these only differ by the fixed scaling factor, and the relative orientation of the endoscope apparatuses or of the end effectors also corresponds to that of the respectively assigned control elements or manual control elements. In particular, the actuator mechanism of the manipulator apparatus is automatically actuated accordingly by the electronic controller. What this can achieve is that the endoscope apparatuses can be operated in a particularly simple and intuitive manner by a user of the remote manipulator system. By way of example, the control elements can be movable in a model space that reproduces the body-internal cavity. Further, an endoscopic image of the cavity or of an operating region, recorded by an endoscope optical unit, can be displayed in such a way that the location of the control elements in the image corresponds to the respectively assigned endoscope apparatuses in the cavity or in the operating region. Provision can also be made for a plurality of users to be able to carry out the method simultaneously.

In a particularly preferred fashion, provision is made for one of the manual control elements to be blocked, in particular blocked automatically, in a current position and orientation if it is let go by a user. This can prevent an uncontrolled movement of the assigned endoscope apparatus.

It is understood that the features specified above and this features yet to be explained below are usable not only in the respectively specified combination, but also in other combinations or on their own, without departing from the scope of the present invention.

BRIEF DESCRIPTION OF THE FIGURES

Further aspects of the invention emerge from the following description of preferred exemplary embodiments and from the attached drawing. In the drawing.

DETAILED DESCRIPTION

Figure 1:
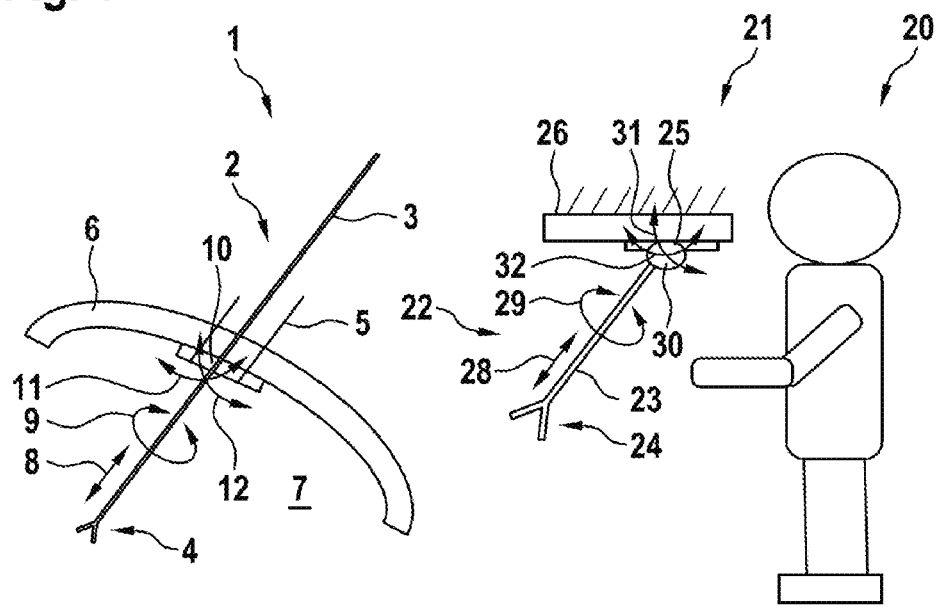
FIG. 1 shows an exemplary embodiment of a remote manipulator system according to the invention in a schematic partial illustration.

FIG. 1 illustrates components of a remote manipulator system according to the invention in exemplary fashion. A manipulator apparatus 1 comprises an endoscopic instrument 2 which has an elongate shaft 3, at the tip of which a tool 4 is arranged. The endoscopic instrument 2 is introduced into the abdominal cavity 7 via a trocar tube 5 through the abdominal wall 6 of the patient, said abdominal cavity having been enlarged by insufflation with a gas in order to provide a sufficient work space for the tool 4. As indicated in FIG. 1, the endoscopic instrument 2 can be displaced in the direction of the longitudinal axis of the shaft 3 (indicated by arrow 8 in FIG. 1), can be rotated about the longitudinal axis (arrow 9) and can be pivoted along two axes about a pivot point 10 defined by the trocar tube 5 (arrows 11, 12).

The endoscopic instrument 2 can be controlled by a user 20 by means of an operating apparatus 21. The operating apparatus comprises a control element 22 with an elongate shaft 23, at the end of which a manual control element 24 is arranged. The shaft 23 is mounted in a longitudinally displaceable manner in a two-axis rotary joint 25. The rotary joint 25 is fastened to a holder 26. The manual control element 24 can be grasped by the user 22 with one hand and can be moved in a model space 27. As indicated in FIG. 1, the control element 22 has the same degrees of freedom of the endoscopic instrument 2, namely a displacement in the direction of the longitudinal axis of the shaft 23 (arrow 28), a rotation about the longitudinal axis of the shaft 23 (arrow 29) and pivoting about the pivot point 30 defined by the rotary joint 25 (arrows 31, 32).

The manipulator apparatus 1 has an actuator mechanism for moving the endoscopic instrument 2 and the operating apparatus comprises sensors for detecting the movement of the control element 22 (not illustrated). A controller, likewise not illustrated, is configured to control the movement of the endoscopic instrument 2 according to the movement of the control element 22. Further, the tool 4 of the endoscopic instrument 2 can be actuated by actuating an actuation element on the manual control element 24.

In terms of its mechanical structure, in particular in view of the movement degrees of freedom and the actuation possibilities, the control element 22 corresponds to the endoscopic instrument 21. In the illustrated example, the corresponding movements of the endoscopic instrument 2 can be controlled by an axial movement of the shaft 23 in both directions (arrow 28), by a rotation about the longitudinal axis (arrow 29) and by pivot movements about two axes of rotation that extend through the pivot point 30 (arrows 31, 32), and by opening and closing the jaw parts of the manual control element 24. In the case of instruments with a shaft that can be angled once or multiple times, the manual control element 24 can likewise be able to be angled in a corresponding manner for the purposes of controlling corresponding angling. If an endoscope optical unit should be controlled in place of the endoscopic instrument 2, provision can be made of a corresponding control element without manual control elements or, for an endoscope optical unit with a lateral viewing direction, provision can be made of a fixed manual control element with a corresponding angle in relation to the shaft (not illustrated).

According to the exemplary embodiment described here, the manipulator apparatus 1 has at least two endoscopic instruments 2 and the operating apparatus has at least two control elements 22, wherein each control element 22 is respectively assigned to an endoscopic instrument 2. This is illustrated in exemplary fashion in the following figures.

Figure 2:
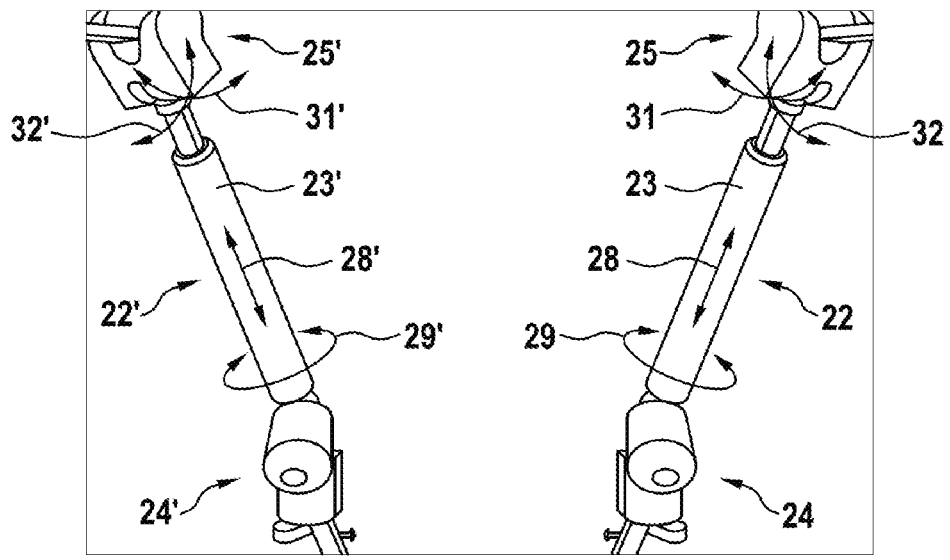
FIG. 2 shows two control elements of a remote manipulator system according to the invention according to one exemplary embodiment.

FIG. 2 shows two control elements 22, 22', wherein details for realizing the described degrees of freedom are illustrated in exemplary fashion. For the purposes of a displacement in the longitudinal direction (arrows 28, 28'), the shafts 23, 23' each have a telescopic configuration. For the purposes of a rotation about the longitudinal axis of the shaft 23, 23' (arrows 29, 29'), the manual control element 24, 24' is respectively arranged in rotatable fashion at the distal end of the shaft 23, 23'. Further, two rotary joints 25, 25' are illustrated in symbolic fashion in FIG. 2, said rotary joints facilitating a two-axis pivot movement (arrows 31, 31', 32, 32') and being embodied in the shown example by two single-axis rotary joints that build on one another. Corresponding linear or rotary encoders (not illustrated) are integrated for the purposes of detecting the respective longitudinal displacement (arrows 28, 28') and the pivot movements (arrows 29, 29', 31, 31', 32, 32').

Figure 3:
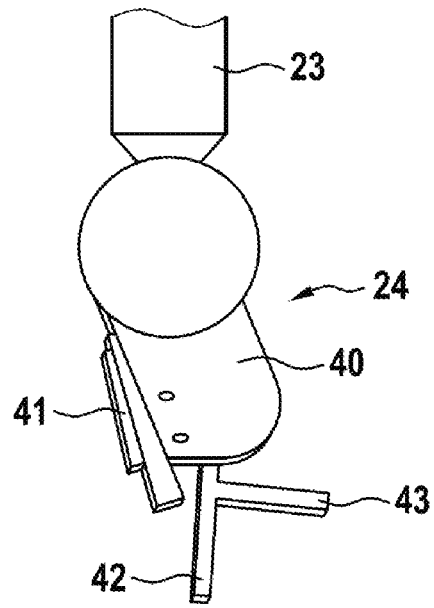
FIG. 3 shows a manual control element of a control element according to FIG. 2 in a magnified illustration.

The manual control element 24 is shown in magnified fashion in FIG. 3. The manual control element 24 has a main body 40 with a grip area 41 and, lying opposite thereto, a pivot lever 42 with a finger ring 43. The hand control element 24 can be grasped by one hand, with a finger resting against the grip area 41 and a further finger being placed through the finger ring 43. Consequently, the pivot lever 42 can be moved by means of the two fingers, the movement of said pivot lever likewise being detected by means of a sensor and being converted into a corresponding movement of the jaw parts of the tool 4 by the controller (see FIG. 1). Further, the manual control element 24 may have a further pivot axis, by means of which the main body 40 is pivotable in relation to the shaft 23, as a result of which an angle of the tool 4 in relation to the shaft 3 of the endoscopic instrument 2 can be controlled. When operating the remote manipulator system, the user holds the manual control element 24 in one hand and can control both the movement of the shaft 3 of the instrument 2 and the actuation of the tool 4 therewith.

Figure 4:
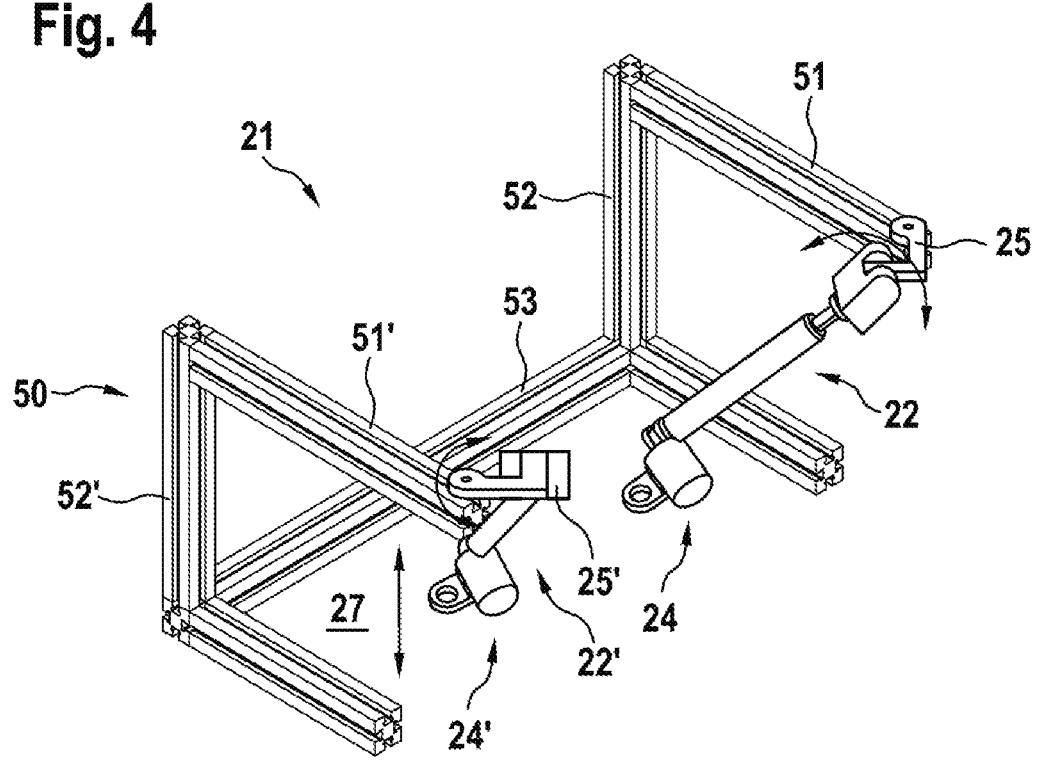
FIG. 4 shows an operating apparatus having the control elements according to FIG. 2.

FIG. 4 schematically illustrates the structure of the operating apparatus 21. The two-axis rotary joints 25, 25' of the control elements 22, 22' are arranged on a frame 50 in adjustable fashion, said frame comprising a plurality of guides 51, 51', 52, 52', 53, which are fastened so as to be displaceable against one another, with the rotary joints 25, 25' likewise being arranged in displaceable fashion on the guides 51, 51'. The operating apparatus 21 can be set by means of the adjustable frame 50 in such a way that the relative position of the pivot points 30 defined by the rotary joints 25, 25' corresponds to the relative position of the pivot points 10 of two endoscopic instruments 2 defined by the trocar tubes 5 inserted into the abdominal wall 6 of a patient (see FIG. 1). The spatial alignment of the control elements 22, 22' and of the manual control elements in relation to one another corresponds to the spatial alignment of the endoscopic instruments controlled thereby and of the tools respectively arranged at the distal end. Since the movement of the endoscopic instruments also corresponds to that of the control elements 22, 22', the arrangement of the control elements 22, 22' and of the manual control elements corresponds to one another, even after carrying out a movement of the arrangement of the assigned endoscopic instruments and the respective tools. Consequently, the arrangement in the model space 27 always represents an image of the arrangement in the work space. This significantly simplifies the intuitive operation of the endoscopic instruments 2 by means of the manipulator apparatus 1 by moving the manual control elements 24, 24' in the model space 27.

Figure 5:
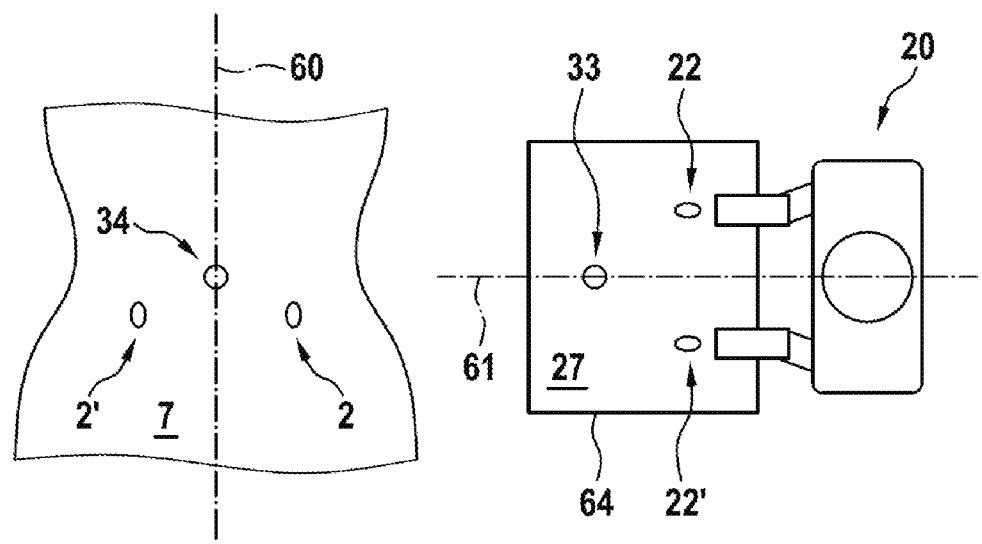
FIG. 5 shows an operating apparatus with a model space and a work space of a remote manipulator system according to the invention in a symbolic illustration.

FIG. 5 symbolically illustrates the operating situation. With one hand in each case, a user 20 grasps the manual control elements of the control elements 22, 22' and said user can control the movement of the endoscopic instruments 2, 2' in the work space, which is the abdominal cavity 7 of the patient that has been enlarged in the illustrated example by gas insufflation, by moving said control elements in the model space 27. The model space 27 reproduces the spatial conditions in the intracorporal work space. FIG. 5 additionally indicates a control element 33 for an endoscope optical unit 34, the position of which in the work space is likewise indicated. The movement of the endoscope optical unit 34 within the work space can be controlled in corresponding fashion by manually moving the control element 33 in the model space 27, in particular by way of an axial displacement, a pivot movement about a pivot point and a rotational movement about a longitudinal axis.

The endoscope optical unit 34 allows an image of the work space within the abdominal cavity 7 to be recorded and to be displayed for the user 20 on a monitor 64, which is arranged below the model space 27. Here, the presentation is implemented in such a way that an axis 60 in the abdominal cavity 7 is mapped onto an operating axis 61 in the model space 27, and the manipulator apparatus is actuated in such a way that a movement of the control elements 22, 22', 33 relative to the operating axis 61 is converted into a corresponding movement of the endoscopic instruments 2, 2' or of the endoscope optical unit 34 relative to the axis 60. The arrangement of the control elements 22, 22', 33 in relation to one another and relative to the operating axis 61 corresponds to the arrangement of the endoscopic instruments 2, 2' and of the endoscope optical unit 34 relative to one another and relative to the axis 60.

Figure 6A:
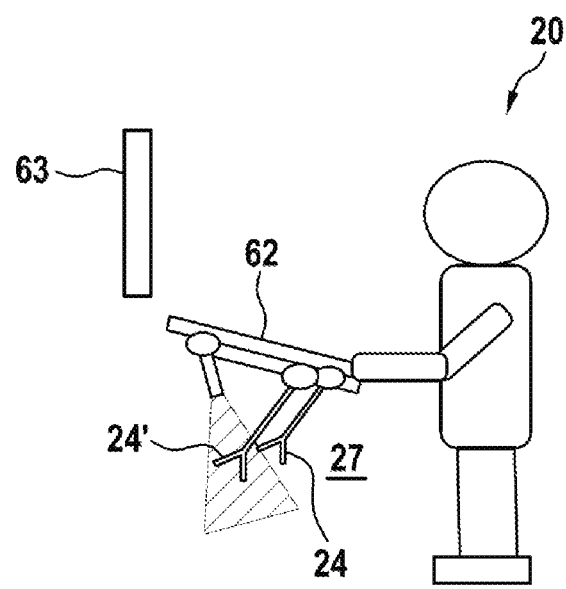
FIGS. 6a to 6c show operating apparatuses of the remote manipulator system according to the invention in different embodiments.
Figure 6B:
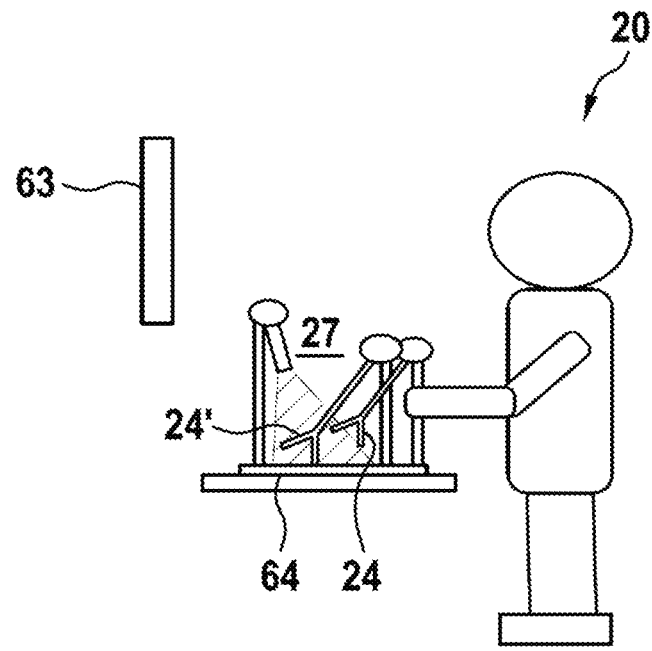
Figure 6C:
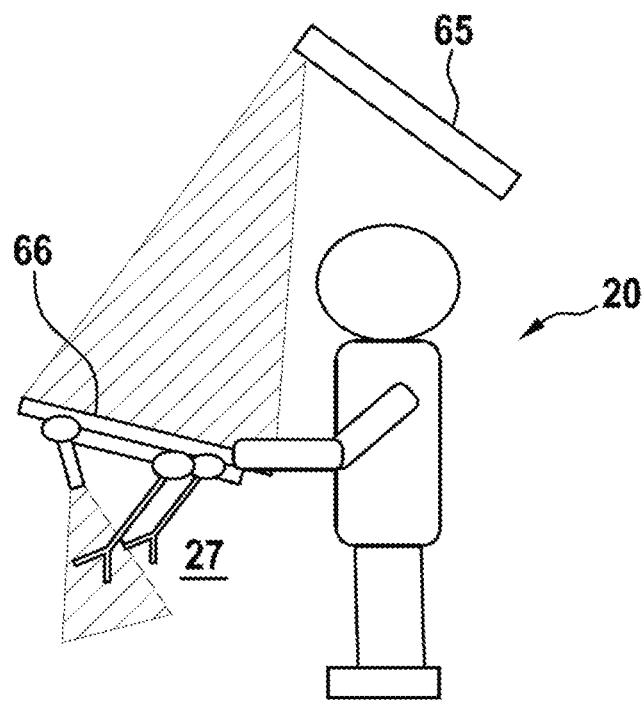

FIGS. 6a to 6c each schematically show a side view of how an image of the work space can be presented to the user in a suitable manner in order to simplify a surgical intervention being carried out. According to FIG. 6a, a partly transparent monitor 62 can be arranged above the model space 27, for example, said monitor displaying an image of the work space recorded by the endoscope optical unit 34 (see FIG. 5 as well as 7 and 8). In the embodiment illustrated in FIG. 6b, which corresponds to that shown in FIG. 5, a monitor 64 is arranged below the model space 27. Additionally, a further monitor 63 may be present. As shown in FIG. 6c, a projector 65 may also be provided in place of a monitor, said projector projecting the image onto a projection surface 66 above the model space 27. In all cases, the display is implemented in such a way that the movement of the control elements 22, 22' by the manual control elements 24, 24' in the model space 27 corresponds to the movement of the endoscopic instruments 2, 2' and the corresponding tools 4 in the work space.

Figure 7:
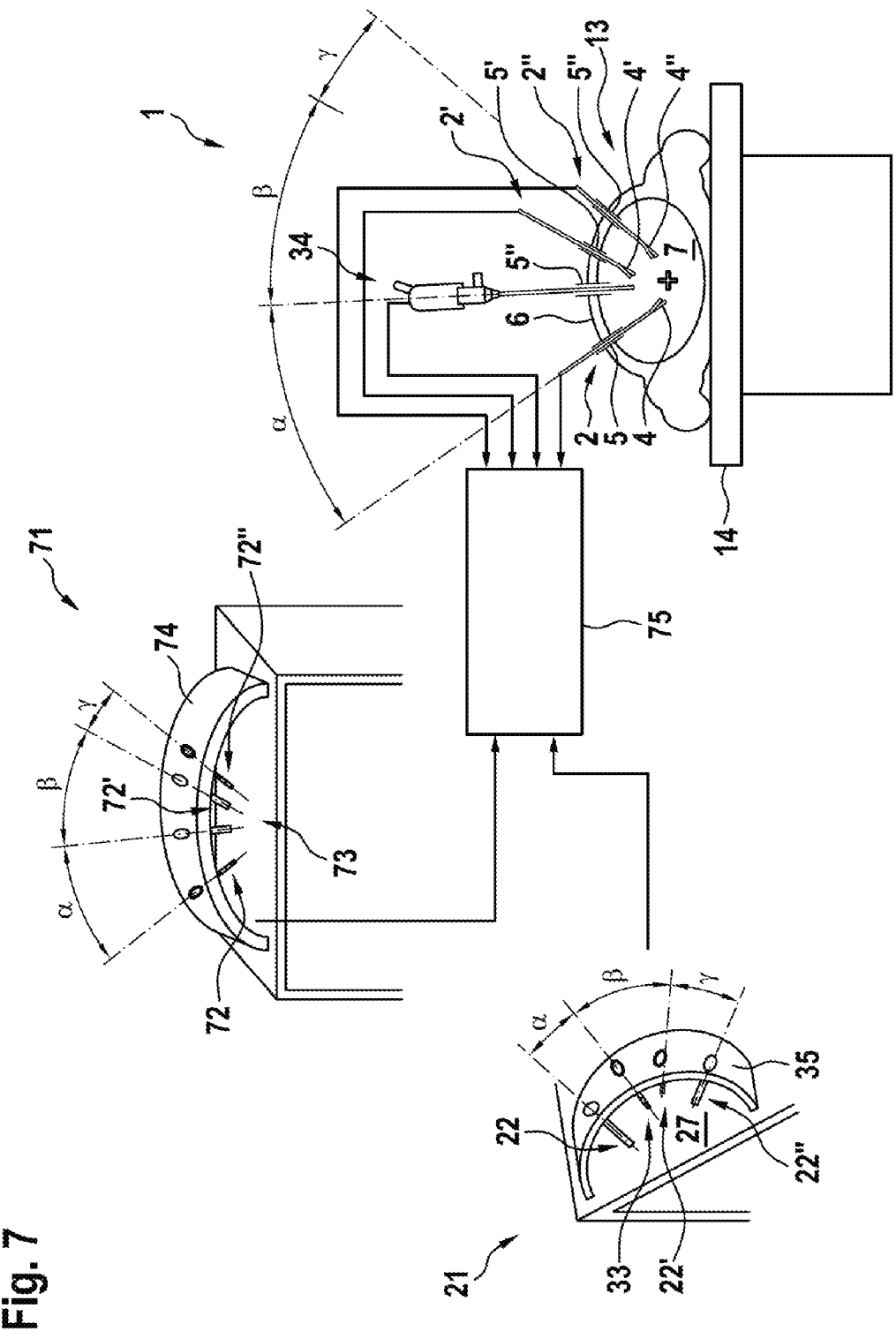
FIG. 7 shows an exemplary embodiment of a remote manipulator system according to the invention in a schematic illustration.

FIG. 7 illustrates, in exemplary fashion, a remote manipulator system according to the invention in a schematic form. A multiplicity of endoscopic instruments 2, 2', 2" have been introduced through corresponding trocar tubes 5, 5', 5" into the abdominal cavity 7 of a patient 13 who is lying on an operating table 14. Further, an endoscope optical unit 34 has been introduced into the abdominal cavity 7 through a further trocar tube 5'". The movement of the endoscopic instruments 2, 2', 2" and the endoscope optical unit 34 and the actuation of the tools 4, 4', 4" of the endoscopic instruments 2, 2', 2" is brought about by an actuator mechanism, not illustrated, which is controlled by a controller 75. The actuator mechanism is controlled in such a way that the passage points of the trocar tubes 5, 5', 5", 5'" through the abdominal wall 6, i.e., the trocar points, form pivot points for pivot movements of the instruments 2, 2', 2" and of the endoscope optical unit 34. The controller 75 is controlled, in turn, by way of two operating apparatuses 21, 71, which each comprise appropriate control elements 22, 22', 22'", 72, 72', 72" for the endoscopic instruments 2, 2', 2". Likewise, provision is made for a control element 33, 73 in each case, said control element being assigned to the endoscope optical unit 34 and a movement of the endoscope optical unit 34 being able to be controlled thereby. The spatial arrangement of the pivot points, about which the control elements 22, 22', 22", 73 can be pivoted, corresponds to the spatial arrangement of the trocar points in the abdominal wall 6. In particular, the distances of the pivot points of the control elements 22, 22', 22", 73 from one another are set like the spacings of the trocar points of the trocar tubes 5, 5', 5", 5'" of the respectively assigned instruments 2, 2', 2" and of the endoscope optical unit 34. As shown in FIG. 7, the controller apparatus 75 is configured in such a way that the angles α, β, γ between the control elements 2, 33, 2', 2" and 72, 73, 72', 72" correspond to the angles formed by the endoscopic instruments 2, 2', 2" and the endoscope optical unit 34 with one another. Likewise, an insertion length of the endoscopic instruments 2, 2', 2" and of the endoscope optical unit 34 into the abdominal cavity 7 is determined as corresponding to a length of the control elements 22, 33, 22', 22" and 72, 73, 72', 72". The rotary joints that define the pivot points are each held in an arched support area 35, 74, the form of which approximately corresponds to the form of the abdominal wall 6; the support areas 35, 74 also facilitate an adjustment of the pivot points within the respective support area 35, 74 (not illustrated). The operating apparatuses 21, 71 can be embodied as operating consoles, wherein a user can operate two control elements on each operating console in each case. A monitor 62, 64 or a projection surface 66 can be arranged on a top side of the operating console in each case (see FIGS. 6a to 6c; not illustrated in FIG. 7).

Figure 8:
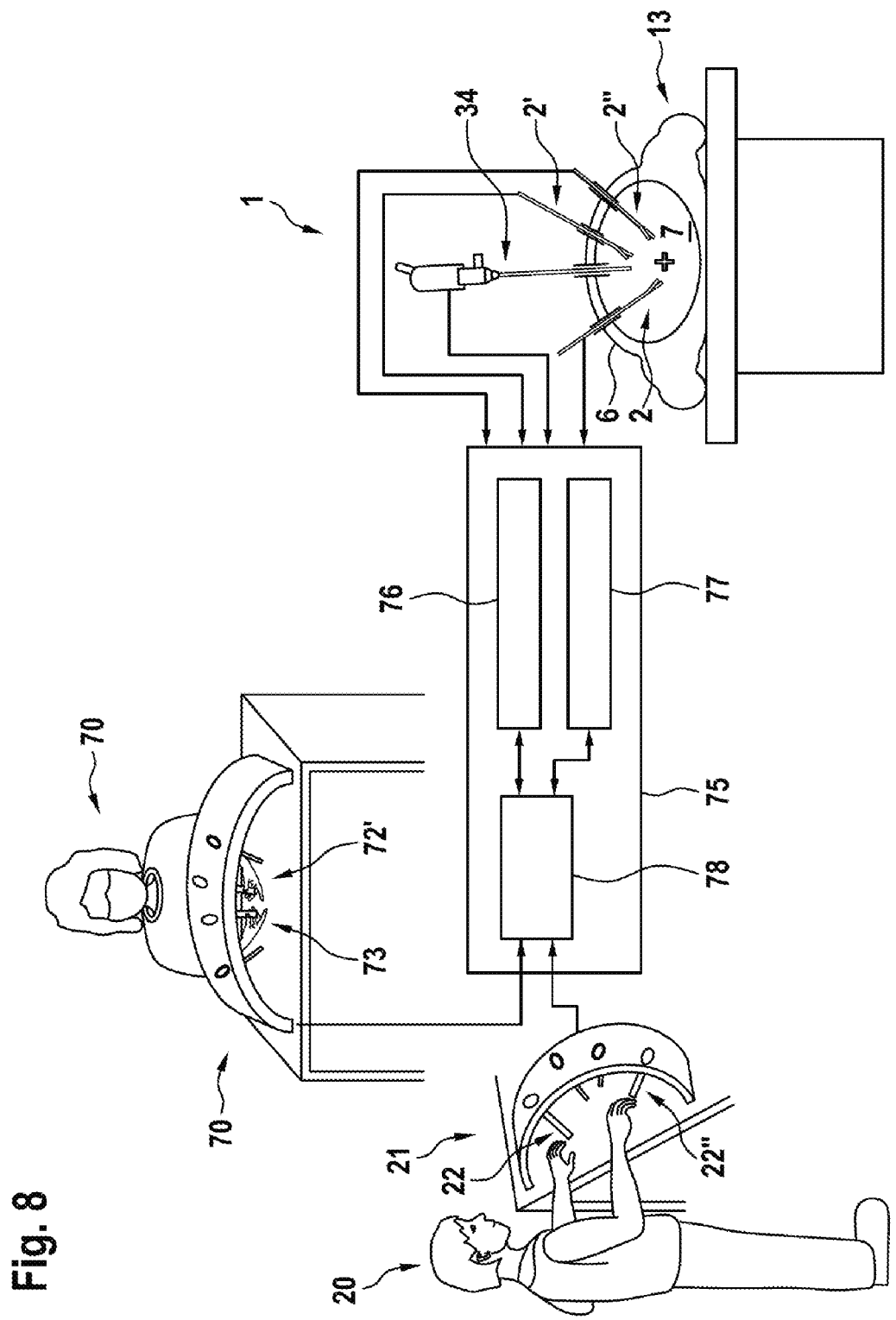
FIG. 8 shows the operation of the remote manipulator system according to FIG. 7 in a schematic illustration.

The operation of the remote manipulator system is shown once again in FIG. 8 with two users 20, 70. In particular, it could be advantageous for a first user 20 to control two endoscopic instruments 2, 2" on the operating apparatus 21 and operate the control elements 22, 22' assigned thereto, while a further user 70 controls a further endoscopic instrument 2' and the endoscope optical unit 34 by virtue of operating the control elements 72', 73 of the second operating apparatus 71 assigned thereto. The corresponding control elements on the respective other operating console can be deactivated, and so only one control element is active for each instrument 2, 2', 2" or for the endoscope optical unit 34 at any one time, or said corresponding control elements on the respective other operating console can be movable in motor-driven fashion such that the spatial arrangement of all control elements 2, 2', 2", 33, 72, 72', 72", 73 on both operating apparatuses 21, 71 is always the same. Further, FIG. 8 indicates that the control device 75 comprises a manipulator control unit 76, which actuates the manipulator apparatus for the purposes of holding and moving the instruments 2, 2', 2" and the endoscope optical unit 34. Furthermore, the controller 75 comprises an image processing unit 77 for actuating the endoscope optical unit 34 and for processing the image recorded by the endoscope optical unit 34 for a suitable illustration on the monitors 62, 64 or by means of the projector 65 (see FIGS. 6a to 6c). Further, the controller 75 comprises a central control unit 78, which controls the interaction of the manipulator control unit 76, the image processing unit 77 and the operating apparatuses 21, 71.

As may be identified from FIGS. 7 and 8, the structure of the operating apparatuses 21, 71 with the control elements 22, 22', 22", 33 and 72, 72', 72", 73, respectively, allows the users 20, 70 to immediately see which movements can be carried out by the endoscopic instruments 2, 2', 2" and the endoscope optical unit 34. Since the control elements 22, 22', 22", 33 and 72, 72', 72", 73 have the same spatial relationship to one another as the endoscopic instruments 2, 2', 2" and the endoscope optical unit 34, these also have the same degrees of freedom. Thus, this can easily avoid, for instance, carrying out those control movements by the control elements 22, 22', 22", 33 and 72, 72', 72", 73 which cannot be executed in the work space by the endoscopic instruments 2, 2', 2" and the endoscope optical unit 34 controlled thereby.

For the sake of clarity, not all reference signs have been illustrated in all figures. Reference signs not explained in relation to one figure have the same meaning as in the remaining figures.

A remote manipulator system according to the invention for carrying out manipulations in a body-internal cavity comprises a manipulator apparatus with a motor-driven actuator mechanism for moving at least two endoscope apparatuses that are insertable through a respective access opening into the body-internal cavity, said endoscope apparatuses each having an elongate shaft 3, wherein the at least two endoscope apparatuses are each displaceable along a longitudinal direction and pivotable about a pivot point 10 defined by the respective access opening, an operating apparatus 21, 71 with at least two control elements 22, 22', 22", 33, 72, 72', 72", 73, which each have an elongate shaft 23, 23', wherein the at least two control elements 22, 22', 22", 33, 72, 72', 72", 73 are each, in manual fashion, displaceable in the direction of a longitudinal axis and pivotable about a pivot point 30, and a controller 75 which is embodied to detect a respective longitudinal displacement and pivot movement of the at least two control elements 22, 22', 22", 33, 72, 72', 72", 73 and actuate the manipulator apparatus 1 in such a way that the movements of the endoscope apparatuses correspond to those of the at least two control elements 22, 22', 22", 33, 72, 72', 72", 73, wherein the operating apparatus 21, 71 is embodied in such a way that a relative position of the pivot points 30 of the control elements 22, 22', 22", 33, 72, 72', 72", 73 is adjustable.

LIST OF REFERENCE SIGNS

1 Manipulator apparatus
2, 2', 2" Instrument
3 Shaft
4, 4', 4" Tool
5, 5', 5", 5, Trocar tube
6 Abdominal wall
7 Abdominal cavity
8 Arrow
9 Arrow
10 Pivot point
11 Arrow
12 Arrow
13 Patient
14 Operating table
20 User
21 Operating apparatus
22, 22', 22" Control element
23, 23' Shaft
24, 24' Manual control element
25, 25' Rotary joint
26 Holder
27 Model space
28, 28' Arrow
29, 29' Arrow
30 Pivot point
31, 31' Arrow
32, 32' Arrow
33 Control element
34 Endoscope optical unit
35 Support area
40 Main body
41 Grip area
42 Pivot lever
43 Finger ring
50 Frame
51, 51' Guide
52, 52' Guide
53, 53' Guide
60 Axis
61 Operating axis
62 Monitor
63 Monitor
64 Monitor
65 Projector
66 Projection surface
70 User
71 Operating apparatus
72, 72', 72" Control element
73 Control element
74 Support area
75 Controller
76 Holding unit
77 Image processing unit
78 Central control unit

The invention claimed is:

1. A remote manipulator system configured to carry out manipulations in a body-internal cavity of a human or animal body, comprising a manipulator apparatus with a motor-driven actuator mechanism configured to move at least two endoscope apparatuses that are insertable through a respective access opening into the body-internal cavity, said endoscope apparatuses each having an elongate shaft, wherein the at least two endoscope apparatuses are each, by the actuator mechanism, displaceable along a longitudinal direction of the shaft and pivotable about a pivot point defined by the respective access opening, an operating apparatus with at least two control elements, which each have an elongate shaft, wherein the at least two control elements are each, in manual fashion, displaceable in the direction of a longitudinal axis of the shaft and pivotable about a respective pivot point, and an electronic controller configured to detect a respective longitudinal displacement and a respective pivot movement of the at least two control elements and actuate the manipulator apparatus in such a way that the movements of the at least two endoscope apparatuses correspond to those of the at least two control elements, wherein the operating apparatus is configured such that a relative position between the pivot points of the at least two control elements is adjustable by a user to match a corresponding spatial relationship between the pivot points of the at least two respective endoscope apparatuses.

2. The remote manipulator system according to claim 1, wherein the spatial relationship of the pivot points of the at least two control elements is manually adjustable.

3. The remote manipulator system according to claim 1, wherein the manipulator apparatus is configured to detect the relative position of the pivot points of the at least two endoscope apparatuses, in that the relative position of the pivot points of the at least two control elements is adjustable in motor-driven fashion and in that the controller is configured in such a way that the pivot points of the control elements are set in a manner corresponding to the detected relative position of the pivot points of the endoscope apparatuses.

4. The remote manipulator system according to claim 1, wherein the at least two endoscope apparatuses are rotatable about the respective longitudinal axis of their shaft, in that the at least two control elements are each rotatable in manual fashion about the longitudinal axis of their shaft and in that the electronic controller is embodied to detect a respective rotation about the longitudinal axis of the shaft of the at least two control elements and actuate the manipulator apparatus in such a way that the endoscope apparatuses are rotated about a respective longitudinal axis of their shaft in a manner corresponding to the rotation of the control elements.

5. The remote manipulator system according to claim 1, wherein a tool is arranged at a distal end of at least one endoscope apparatus, said tool having at least one actuation degree of freedom, and in that a control element assigned to this endoscope apparatus has a manual control element at the distal end of its shaft, said manual control element being embodied to correspondingly actuate the tool.

6. The remote manipulator system according to claim 1, wherein the operating apparatus has a blocking mechanism for blocking the at least two control elements.

7. The remote manipulator system according to claim 6, wherein the blocking mechanism is automatically activatable for the purposes of blocking a control element when the latter has not been grasped, or has been let go, by a user.

8. The remote manipulator system according to claim 1, wherein the manipulator apparatus is embodied to detect a size and form of the body-internal cavity and in that the electronic controller and the operating apparatus are embodied in such a way that the movement range of the at least two control elements is restricted in accordance with the detected size and form of the body-internal cavity.

9. The remote manipulator system according to claim 1, wherein the operating apparatus has a plurality of calibration marks.

10. The remote manipulator system according to claim 1, wherein the remote manipulator system has at least one further operating apparatus.

11. A method for operating a remote manipulator system comprising a manipulator apparatus with a motor-driven actuator mechanism for moving at least two endoscope apparatuses that are insertable through a respective access opening into a body-internal cavity of a human or animal body, said endoscope apparatuses each having an elongate shaft, wherein the at least two endoscope apparatuses are each, by means of the actuator mechanism, displaceable along a longitudinal direction of the shaft and pivotable about a pivot point defined by the respective access opening, said remote manipulator system furthermore comprising an operating apparatus with at least two control elements, which each have an elongate shaft, wherein the at least two control elements are each, in manual fashion, displaceable in the direction of a longitudinal axis of the shaft and pivotable about a respective pivot point, said method including the steps of:

setting the pivot points of the at least two control elements to correspond spatially to the spatial relationship of the pivot points of the endoscope apparatuses, detecting a respective longitudinal displacement and a respective pivot movement of the at least two control elements, and actuating the manipulator apparatus in such a way that a movement of the at least two endoscope apparatuses corresponds to that of the at least two control elements.

12. The method according to claim 11, wherein one or more manual control elements are blocked in a current position and orientation when it is let go by a user.

13. A remote manipulator system configured to carry out manipulations in a body-internal cavity of a human or animal body, comprising:

a manipulator system including a motor-driven actuator mechanism configured to move at least two endoscope apparatuses that are insertable through a respective access opening into the body-internal cavity, the endoscope apparatuses each having an elongate shaft, wherein the at least two endoscope apparatuses are each, by the actuator mechanism, displaceable along a longitudinal direction of the shaft and pivotable about a pivot point defined by the respective access opening, an operating apparatus with at least two control elements, which each have an elongate shaft, wherein the at least two control elements are each, in manual fashion, displaceable in the direction of a longitudinal axis of the shaft and pivotable about a respective pivot point, and an electronic controller configured to detect a respective longitudinal displacement and a respective pivot movement of the at least two control elements and actuate the manipulator system in such a way that the movements of the at least two endoscope apparatuses correspond to those of the at least two control elements, wherein the operating system is configured such that a relative position between the pivot points of the at least two control elements is adjustable by a user to match a relative position between the pivot points defined by the respective access opening of the at least two respective endoscope apparatuses.

14. The remote manipulator system according to claim 13, wherein the spatial relationship of the pivot points of the at least two control elements is manually adjustable.

15. The remote manipulator system according to claim 13, wherein the manipulator apparatus is configured to detect the relative position of the pivot points of the at least two endoscope apparatuses, in that the relative position of the pivot points of the at least two control elements is adjustable in motor-driven fashion and in that the controller is configured in such a way that the pivot points of the control elements are set in a manner corresponding to the detected relative position of the pivot points of the endoscope apparatuses.

16. The remote manipulator system according to claim 13, wherein the operating apparatus has a movement restrictor configured to limit movement the at least two control elements.

17. The remote manipulator system according to claim 16, wherein the movement restrictor is automatically activatable to block a control element if the control element has not been grasped, or has been let go of, by a user.

* * * * *